(12) United States Patent
Pham et al.

(10) Patent No.: US 12,023,070 B2
(45) Date of Patent: Jul. 2, 2024

(54) SACRAL-ILIAC STABILIZATION SYSTEM

(71) Applicant: GLOBUS MEDICAL, INC., Audubon, PA (US)

(72) Inventors: Khiem Pham, Chalfont, PA (US); Mark Salzberger, Sinking Spring, PA (US)

(73) Assignee: Globus Medical, Inc., Audubon, PA (US)

(*) Notice: Subject to any disclaimer, the term of this patent is extended or adjusted under 35 U.S.C. 154(b) by 95 days.

(21) Appl. No.: 17/499,197

(22) Filed: Oct. 12, 2021

(65) Prior Publication Data

US 2022/0039841 A1    Feb. 10, 2022

Related U.S. Application Data

(63) Continuation of application No. 16/448,610, filed on Jun. 21, 2019, now Pat. No. 11,147,596, which is a continuation of application No. 13/189,084, filed on Jul. 22, 2011, now Pat. No. 10,368,919.

(60) Provisional application No. 61/366,815, filed on Jul. 22, 2010.

(51) Int. Cl.
*A61B 17/70* (2006.01)

(52) U.S. Cl.
CPC ...... *A61B 17/7055* (2013.01); *A61B 17/7032* (2013.01)

(58) Field of Classification Search
CPC ............ A61B 17/7055; A61B 17/7059; A61B 17/8066; A61B 17/8061; A61B 17/8057; A61B 17/809
See application file for complete search history.

(56) References Cited

U.S. PATENT DOCUMENTS

| | | |
|---|---|---|
| 4,773,402 A | 9/1988 | Asher et al. |
| 5,084,049 A | 1/1992 | Asher |
| 5,127,912 A | 7/1992 | Ray |
| 5,133,717 A * | 7/1992 | Chopin ............... A61B 17/7055 606/264 |
| 5,147,360 A | 9/1992 | Dubousset |
| 5,300,073 A | 4/1994 | Ray |
| 5,571,102 A | 11/1996 | Cavagna |
| 5,622,652 A | 4/1997 | Kucherovsky |
| 5,993,449 A | 11/1999 | Schlapfer et al. |
| 6,106,526 A | 8/2000 | Harms |
| 6,129,730 A | 10/2000 | Bono et al. |
| 6,132,431 A | 10/2000 | Nilsson |
| 6,187,005 B1 | 2/2001 | Brace et al. |
| 6,197,028 B1 | 3/2001 | Ray |
| 6,458,131 B1 | 10/2002 | Ray |
| 6,485,491 B1 | 11/2002 | Farris |
| 6,520,990 B1 | 2/2003 | Ray |
| 6,648,885 B1 | 11/2003 | Friesem |
| 6,682,532 B2 | 1/2004 | Johnson et al. |
| 6,755,829 B1 | 6/2004 | Bono |

(Continued)

*Primary Examiner* — Julianna N Harvey

(57) ABSTRACT

The present invention provides a sacral-iliac plate having an iliac portion with a first screw hole for receiving a first fastener to secure the iliac portion to the iliac bone. A sacral portion integrated monolithically with the iliac portion is also provided with a second and third screw holes for receiving second and third fasteners to secure the sacral portion to the sacral bone. The sacral portion also includes a tulip for receiving and securing a spinal rod.

14 Claims, 5 Drawing Sheets

(56) References Cited

U.S. PATENT DOCUMENTS

| | | |
|---|---|---|
| 7,081,117 B2 | 7/2006 | Bono |
| 7,128,744 B2 | 10/2006 | Weaver et al. |
| 7,232,441 B2 | 6/2007 | Altarac |
| 7,303,563 B2 | 12/2007 | Poyner |
| 7,455,684 B2 | 11/2008 | Gradel |
| 7,575,588 B2 | 8/2009 | Barker |
| 7,699,872 B2 | 4/2010 | Farris |
| 7,850,719 B2 | 12/2010 | Gournay et al. |
| 8,007,499 B2 | 8/2011 | Piehl |
| 9,585,697 B2 | 3/2017 | Stachniak |
| 9,757,154 B2 | 9/2017 | Donner et al. |
| 9,872,711 B2 | 1/2018 | Haynes et al. |
| 2004/0162558 A1 | 8/2004 | Hegde et al. |
| 2005/0251141 A1* | 11/2005 | Frigg ............... A61B 17/7044 606/291 |
| 2006/0106382 A1 | 5/2006 | Gournay et al. |
| 2006/0195089 A1* | 8/2006 | LeHuec ............ A61B 17/7059 606/280 |
| 2006/0241615 A1* | 10/2006 | Melkent ........... A61B 17/7044 606/281 |
| 2008/0021454 A1* | 1/2008 | Chao ................ A61B 17/7044 606/250 |
| 2008/0125781 A1 | 5/2008 | Hoffman et al. |
| 2008/0140130 A1* | 6/2008 | Chan ................ A61B 17/1782 606/301 |
| 2009/0125067 A1 | 5/2009 | Mazzuca et al. |
| 2010/0082067 A1 | 4/2010 | Kondrashov |
| 2010/0114177 A1 | 5/2010 | Piehl |
| 2010/0312286 A1* | 12/2010 | Dell'Oca .......... A61B 17/8057 606/291 |
| 2012/0022595 A1 | 1/2012 | Pham et al. |
| 2014/0249581 A1 | 9/2014 | Stachniak |

\* cited by examiner

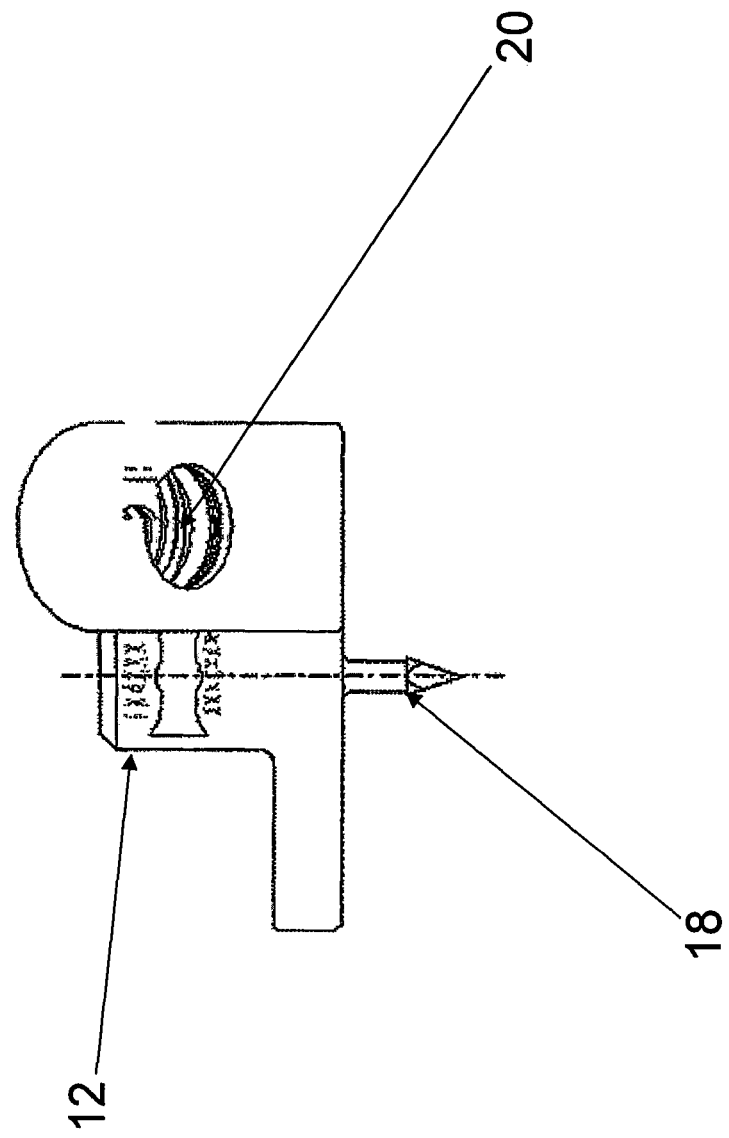

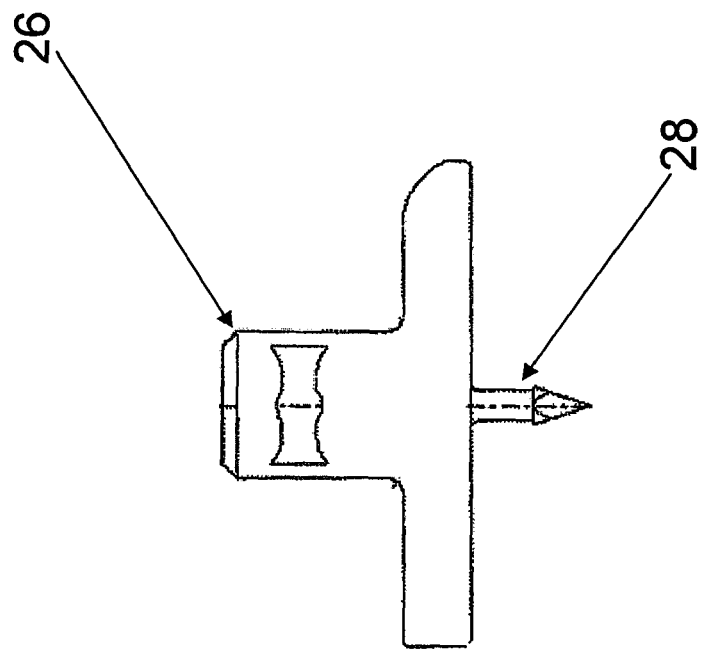
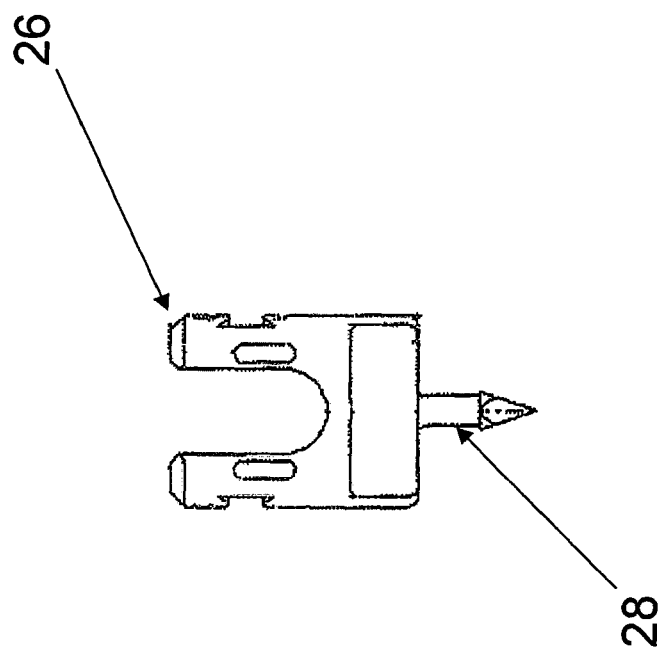

SACRAL-ILIAC STABILIZATION SYSTEM

CROSS REFERENCE TO RELATED APPLICATIONS

This application is a continuation of U.S. application Ser. No. 16/448,610, filed on Jun. 21, 2019, which is a continuation of U.S. Ser. No. 13/189,084, filed on Jul. 22, 2011 (published as U.S. Pat. Pub. No. 2012-0022595), which claims priority to Provisional Application Ser. No. 61/366,815 filed on Jul. 22, 2010, all of which are incorporated herein in their entireties.

FIELD OF THE INVENTION

The present disclosure generally relates to a fixation device for positioning a plate between the sacrum and iliac portion of the human body.

BACKGROUND OF THE INVENTION

Bones and bony structures are susceptible to a variety of weaknesses that can affect their ability to provide support and structure. Weaknesses in bony structures may have many causes, including degenerative diseases, tumors, fractures, and dislocations. Advances in medicine and engineering have provided doctors with a plurality of devices and techniques for alleviating or curing these weaknesses. Typically, weaknesses in the spine are corrected by using devises that fuse one or more vertebrae together. There is a need stabilizing the iliac portion of the human body to the sacrum portion of the vertebrae to provide additional stability.

SUMMARY OF THE INVENTION

The present invention provides a sacral-iliac plate having an iliac portion with a first screw hole for receiving a first fastener to secure the iliac portion to the iliac bone. A sacral portion integrated monolithically with the iliac portion is also provided with a second and third screw holes for receiving second and third fasteners to secure the sacral portion to the sacral bone. The sacral portion also includes a tulip for receiving and securing a spinal rod.

BRIEF DESCRIPTION OF THE DRAWINGS

FIG. 3 is back view of the sacral-iliac plate illustrated in FIG. 1-3;

FIG. 5A is a front view of the sacral-iliac place shown in FIG. 4;

FIG. 5B is a side view of the sacral-iliac plate shown in FIG. 4; and

DETAILED DESCRIPTION OF THE ILLUSTRATED EMBODIMENTS

While it is apparent that the invention disclosed herein is well calculated to fulfill the objects stated above, it will be appreciated that numerous modifications and embodiments may be devised by those skilled in the art.

Figure 1:
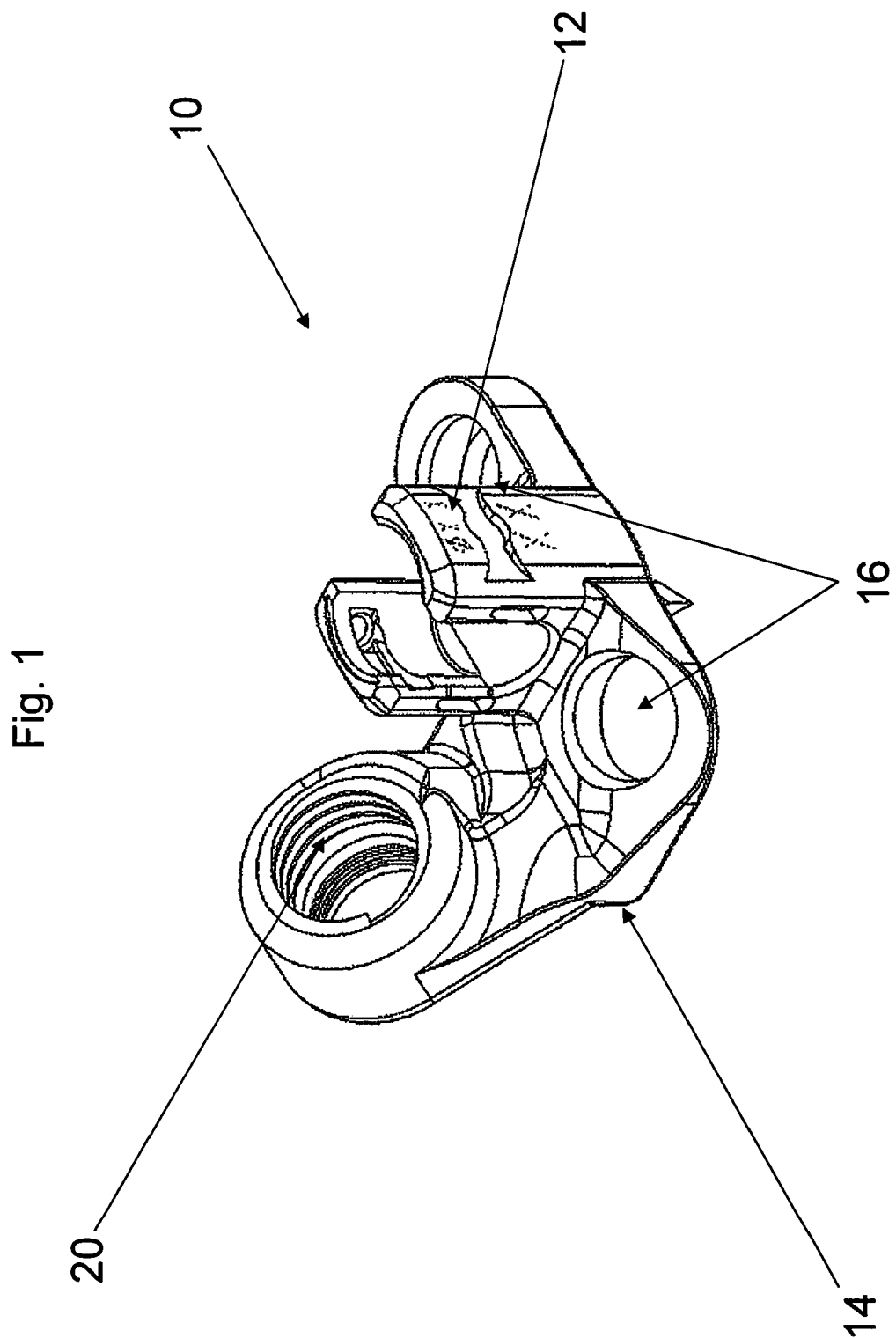
FIG. 1 is a perspective view of a sacral-iliac plate according to one embodiment of the present invention.

FIGS. 1-3 illustrate the sacral-iliac plate according to one embodiment of the present invention. Specifically, the sacral-iliac plate of the present invention enables surgeons the ability to use the plate for various medical conditions such as spondylolisthesis, neuromuscular scoliosis, degenerative lumbosacral joint, and pelvic obliquity.

Turning now to FIG. 1, a sacral-iliac plate 10 is shown. The plate 10 is a unitary plate with an integrated tulip 12 that provides support and stability across the sacral iliac joint configured to receive a spinal rod within the tulip 12. The plate 10 is further configured with an integrated tulip feature which allows the spinal rod to be top loaded.

Figure 2B:
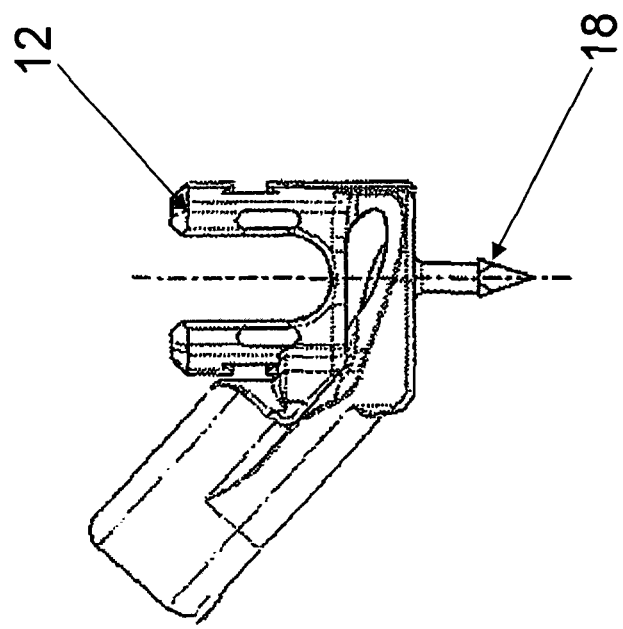
FIGS. 2A and 2B are side views of the sacral-iliac plate of the present invention.
Figure 2A:
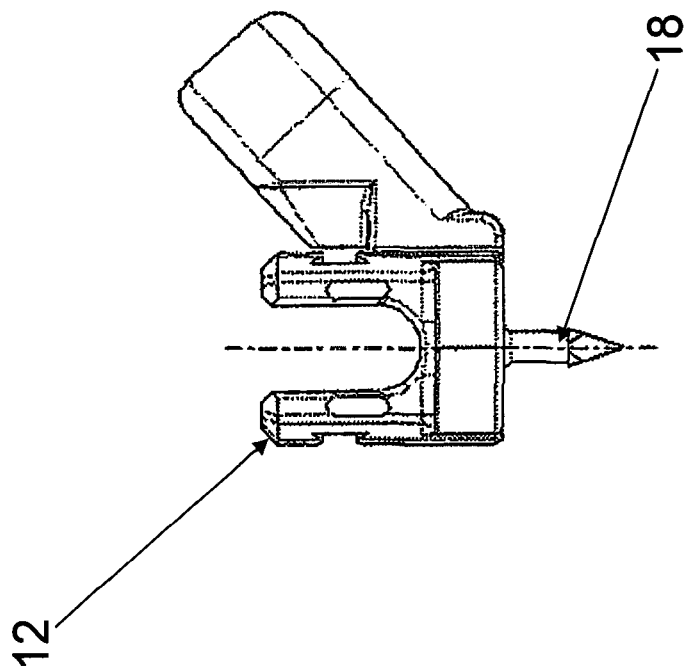

As best seen in the FIGS. 2A and 2B, the sacral iliac plate 12 includes a generally L-shaped body 14 with the integrated tulip head 12 interposed between and generally in line with two sacral holes 16. A sharp prong 18 or barb extends downward from the undersurface to facilitate temporary fixation during installation. The sacral holes 16 are non-threaded holes and are configured to receive screws there through to attach the sacral iliac plate to a sacrum bone of a patient. The tulip head 12 extends upward from the superior surface of the plate body 14 and forms a channel in the direction of the sacral holes 16 for receiving a spinal rod and a cap (not shown) may be used to secure the rod therein. In the embodiment illustrated, the sacral holes 16 are configured to be in-line with the tulip, however, the sacral holes 16 may be offset to accommodate the anatomy of the sacral bone. An iliac portion of the L-shaped body 14 extends laterally outward and angled upwards from a lower portion of the sacral iliac plate 12. The angulation of iliac portion of the plate 12 with respect to the lower portion is generally between 35° to 50° and preferably 40°.

The iliac portion has a threaded hole 20 that is configured to receive a screw therein to fix the iliac portion of the sacral iliac plate to the iliac bone of a patient. The iliac screw head has corresponding threads to mate with the threaded portion of the iliac screw hole 20. It should be noted that although in the present embodiment, the iliac portion of the plate 12 is provided with a threaded hole 20, a non-threaded hole may be utilized.

Figure 4:
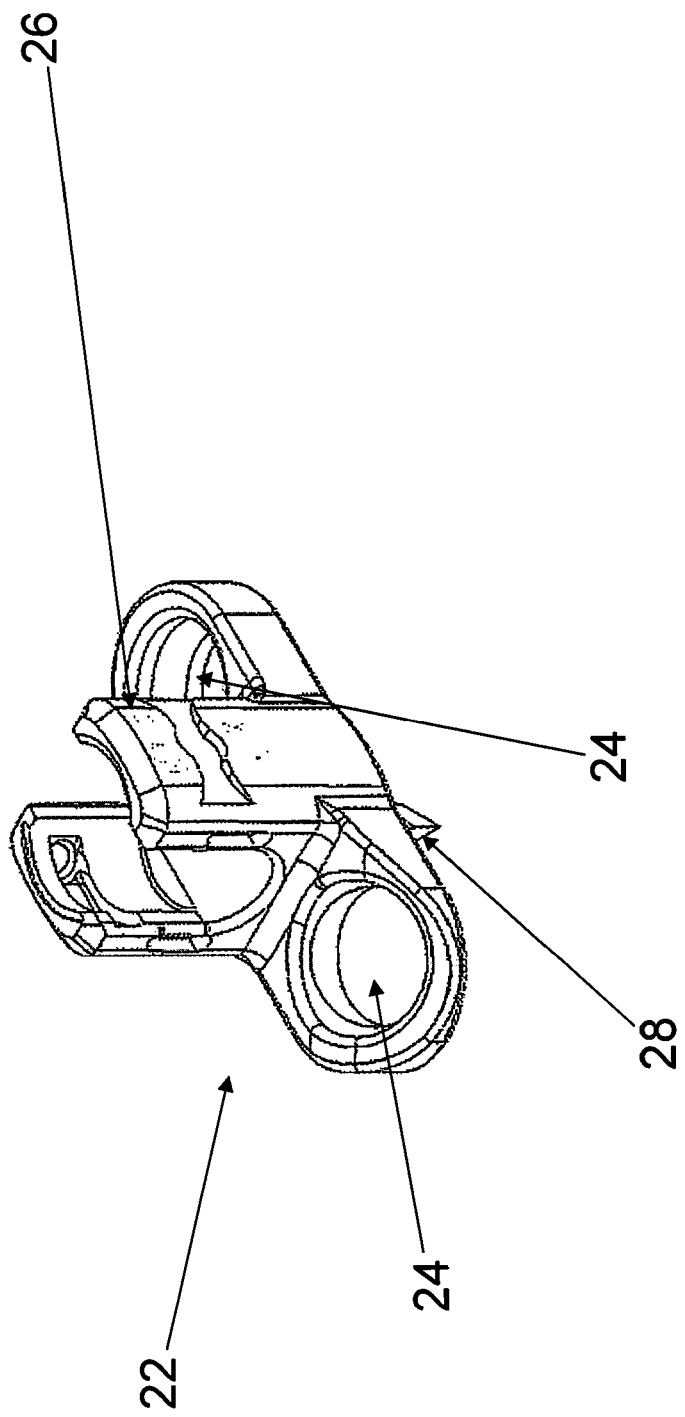
FIG. 4 is a perspective view of another embodiment of a sacral-iliac plate according to the present invention.

FIGS. 4, 5A and 5B illustrate another embodiment of the present invention. In this embodiment, the sacrum plate 22 is provided with two screw holes 24 having a tulip 26 configured between the two screw holes 24. The tulip 26 is designed and configured to receive a spinal rod and a locking cap. The plate is also provided with a sharp prong or barb 28 which extends downward from the undersurface to facilitate temporary fixation during installation. It should be noted that although a single prong is illustrated, multiple prongs may be used to more securely fixate the plate to the sacrum.

The various features and embodiments of the invention described herein may be used interchangeably with other feature and embodiments. Finally, while it is apparent that the illustrative embodiments of the invention herein disclosed fulfill the objectives stated above, it will be appreciated that numerous modifications and other embodiments may be devised by one of ordinary skill in the art. Accordingly, it will be understood that the appended claims are intended to cover all such modifications and embodiments which come within the spirit and scope of the present invention.

The invention claimed is:

1. A sacral plate comprising:
   a main body including:
      a superior hole, the superior hole receives a first screw for insertion into a sacrum;

an inferior hole, the inferior hole receives a second screw;
a tulip disposed between the superior and inferior holes, and having a channel for receiving a rod in a top loading manner;
a sharp prong extending downwardly from an undersurface of the main body and adapted for temporary fixation of the main body to the sacrum,
an iliac portion extending from the main body and having a third hole, the third hole receives an iliac screw to secure the iliac portion to an iliac bone,
wherein the third hole is threaded and a head portion of the iliac screw is threaded for threaded mating,
wherein the channel extends at least partially along a length of the rod towards the superior hole and the inferior hole, and
wherein the main body is integrated monolithically with the iliac portion and the tulip.

2. The sacral plate according to claim 1, wherein the prong extends downwardly from a center of the tulip.

3. The sacral plate according to claim 1, wherein the superior and inferior holes are non-threaded holes to receive the respective first and second screws.

4. The sacral plate according to claim 1, wherein the superior and inferior holes are in line with the tulip.

5. The sacral plate according to claim 1, wherein the tulip is adapted to receive a locking cap for securing the rod within the tulip.

6. The sacral plate according to claim 1, wherein the iliac portion is angled between 35° to 50° with respect to the main body.

7. The sacral plate according to claim 1, wherein the iliac portion is angled at about 40° with respect to the main body.

8. A sacral plate comprising:
a main body including:
a superior hole adapted to receive a first screw for insertion into a sacrum;
an inferior hole adapted to receive a second screw, the superior and inferior holes being non-threaded;
a tulip disposed between the superior and inferior holes, and having a channel for receiving a rod in a top loading manner and in a direction defined by an imaginary line between the superior and inferior holes, and
an iliac portion extending from the main body and having a third hole, the third hole receives an iliac screw to secure the iliac portion to an iliac bone,
wherein the third hole is threaded and the head portion of an iliac screw is threaded for threaded mating,
wherein the channel extends at least partially along a length of the rod towards the inferior hole and the superior hole, and
wherein the main body is integrated monolithically with the iliac portion and the tulip.

9. The sacral plate of claim 8, further comprising a sharp prong extending downwardly from an undersurface of the main body and adapted for temporary fixation of the main body to the sacrum.

10. The sacral plate according to claim 9, wherein the prong extends downwardly from a center point of the tulip.

11. The sacral plate according to claim 8, wherein the superior and inferior holes are in line with the tulip.

12. The sacral plate according to claim 8, wherein the tulip is adapted to securely receive a locking cap above the rod for securing the rod within the tulip.

13. The sacral plate according to claim 8, wherein the tulip includes a pair of walls projecting upwardly from the main body and each wall includes an inner surface that faces the rod and an outer surface having a recess.

14. The sacral plate according to claim 8, wherein the iliac portion is angled between 35° to 50° with respect to the main body.

* * * * *